United States Patent [19]

Letton et al.

[11] Patent Number: 5,286,879
[45] Date of Patent: Feb. 15, 1994

[54] PROCESS FOR THE PREPARATION OF MONO-CONDENSATION DERIVATIVES OF ADIPIC ACID

[75] Inventors: James C. Letton; Larry E. Miller, both of Cincinnati, Ohio

[73] Assignee: The Procter & Gamble Company, Cincinnati, Ohio

[21] Appl. No.: 956,926

[22] Filed: Oct. 5, 1992

[51] Int. Cl.$^5$ .................. C07D 305/00; C07C 229/00; C07C 205/00

[52] U.S. Cl. ..................... 549/231; 560/145; 560/155; 560/170; 560/172; 560/202; 562/439; 562/450; 562/457; 562/507; 562/509; 562/553; 562/590

[58] Field of Search ............... 549/231; 560/172, 190, 560/202, 145, 170, 155; 562/590, 439, 457, 507, 509, 553, 450

[56] References Cited

U.S. PATENT DOCUMENTS

| | | | |
|---|---|---|---|
| 4,251,447 | 2/1981 | Perrin | 549/231 |
| 4,414,397 | 11/1983 | Powell | 549/231 |
| 4,634,551 | 1/1987 | Burns et al. | 252/102 |
| 4,686,063 | 8/1987 | Burns | 252/102 |
| 4,909,953 | 3/1990 | Sadlowski et al. | 252/99 |
| 5,055,218 | 10/1991 | Getty et al. | 252/94 |
| 5,166,407 | 11/1992 | Alul et al. | 560/155 |
| 5,206,432 | 4/1993 | Chou | 562/553 |

FOREIGN PATENT DOCUMENTS

| | | |
|---|---|---|
| 0445096A1 | 9/1991 | European Pat. Off. . |
| 3200044 | 7/1983 | Fed. Rep. of Germany ...... 549/231 |
| 3200065 | 7/1983 | Fed. Rep. of Germany ...... 549/231 |

OTHER PUBLICATIONS

"Studies on Polymerization and Ring Formation. VI. Adipic Anhydride," Julian W. Hill, J. Am. Chem. Society, 1930. vol. 52, pp. 4110-4114.

"Melt Polymerization of Adipic Anhydride (Oxepane-2,7-Dione)," Albertsson et al., J. Macromol. Sci.-Chem., vol. A27(4), 1990, pp. 397-412.

"Polymerization of Oxepan-2,7-Dione in Solution and Synthesis of Block Copolymers of Oxepan-2,7-Dione and 2-Oxepanone," Lundmark et al., J. Macromol. Sci.-Chem., vol. A28(1), 1991, pp. 15-29.

"Adipic Acid," Kirk-Othmer's Encyclopedia of Chemical Technology, vol. 1, 1978, pp. 510-531.

Primary Examiner—Cecilia Tsang
Attorney, Agent, or Firm—Betty J. Zea; Robert B. Aylor; Steven J. Goldstein

[57] ABSTRACT

An improved process for preparing mono-condensation derivatives of adipic acid with fewer steps and better purity is disclosed. In particular, this process comprises: (a) forming relatively concentrated and pure cyclic monomeric adipic anhydride by depolymerization and concentration starting from polymeric adipic anhydride; and (b) adding a condensation reactant having an active hydrogen, e.g., a primary or secondary amine, to said cyclic monomeric adipic anhydride to form the corresponding mono-condensation derivative of adipic acid.

29 Claims, No Drawings

PROCESS FOR THE PREPARATION OF MONO-CONDENSATION DERIVATIVES OF ADIPIC ACID

TECHNICAL FIELD

This invention relates to an improved process for preparing mono-condensation derivatives of adipic acid and, in particular, mono-amido adipic acids. This process comprises: (a) forming relatively concentrated and pure cyclic monomeric adipic anhydride by depolymerization and concentration starting from polymeric adipic anhydride; and (b) adding a condensation reactant having a primary active hydrogen, e.g., a primary or secondary amine, to the cyclic monomeric adipic anhydride to form the corresponding mono-condensation derivative of adipic acid.

BACKGROUND OF THE INVENTION

Mono-amido-condensation derivatives of adipic acid can be used in the synthesis of the corresponding amidoperoxyacids. These peroxyacids are known in the art as bleaching compounds. These compounds provide effective bleaching over a wide range of temperatures, from 5° C. to about 85° C., and are effective for removing stains and/or soils from the surface of textiles, especially dingy soils.

Various processes for making mono-amides of adipic acid and the corresponding peroxyacids are known. For example, the peroxyacids can be prepared by the reaction of the carboxylic acids with hydrogen peroxide in the presence of sulfuric acid. Mono-amide of adipic acid can be synthesized by, first, reacting adipic acid with methanol to form the dimethyl ester. Ammonia, or an amine, is reacted with the dimethyl ester to form a mixture of diamides, monoamides-monoesters, diesters, etc. Unreacted diester and methanol are recycled. Thereafter, this mixture is fractionated to isolate the desired monoamide-monoester. The monoamide-monoester is then selectively hydrolyzed to form the monoamide-acid.

U.S. Pat. No. 4,634,551, Burns et al., issued Jan. 6, 1987, teaches that amido acids can be prepared by the reaction of the corresponding acid chloride with the appropriate amine followed by the precipitation of the resulting amido acid. Stability of the peroxyacids formed thereafter is affected by the resulting chloride impurity, as well as metal contamination.

Because of their high melting points, peroxyacids and their precursors can be purified by precipitation and/or crystallization techniques. However, during crystallization any metal ions present can become entrapped in the crystals.

Moreover, organic acids also have a tendency to scavenge trace quantities of metal ions. Metal ion contamination reduces the stability of peroxyacids because they catalyze the decomposition of peroxyacids. Also, metal ions can affect the melting point of peroxyacids.

One object of the present invention is to improve the current process of making amido acids by reducing the number of reaction steps, by producing higher yields with better purity, and by reducing the number of by-products which need to be recycled.

SUMMARY OF THE INVENTION

The present invention relates to an improved process for preparing mono-condensation derivatives of adipic acid comprising the following steps:
  (a) forming relatively concentrated and pure cyclic monomeric adipic anhydride by depolymerization and concentration starting from polymeric adipic anhydride; and
  (b) adding a condensation reactant having a primary active hydrogen to the cyclic monomeric adipic anhydride to form mono-condensation derivative of adipic acid.

The condensation reactant can, e.g., be selected from the group consisting of: hydrazines; amines; thiol salts; phenoxy salts; alcohols; and mixtures thereof. Preferably, the condensation reactant is a primary or secondary amine having an alkyl group with from 1 to about 20 carbon atoms, more preferably, n-nonyl amine. The process can proceed with or without a catalyst, but preferably the reaction proceeds with from 0.5% to about 2% of zinc acetate catalyst. The ratio of cyclic monomeric adipic anhydride to the condensation reactant is from about 1:1 to about 1:0.7, preferably from about 1:1 to about 1:0.9, more preferably about 1:1.

DETAILED DESCRIPTION OF THE INVENTION

The present invention comprises a process for preparing mono-condensation derivatives of adipic acid comprising the following steps:
  (a) forming relatively concentrated and pure cyclic monomeric adipic anhydride by depolymerization and concentration starting from polymeric adipic anhydride; and
  (b) adding a condensation reactant having a primary active hydrogen to the cyclic monomeric adipic anhydride to form a mono-condensation derivative of adipic acid.

Preferably the linear polymeric adipic anhydride or mixtures containing linear adipic anhydride is formed by the reaction of adipic acid with a material having dehydrating power, preferably acetic anhydride at a molar ratio of from 1:0.75 to about 1:2, and preferably about 1:1, at a temperature, for example, of from about 130° C. to about 140° C., preferably from about 135° C. to about 138° C. Acetic anhydride, also known as acetyl oxide or acetic oxide, has the formula:

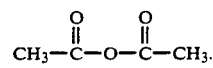

Adipic acid, also known as hexanedioic acid or 1,4-butanedicarboxylic acid, has the formula:

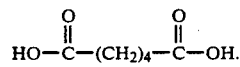

The resulting linear adipic anhydride has the formula:

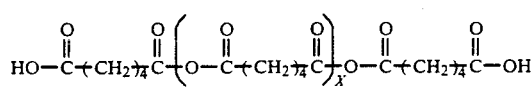

The reaction to form cyclic monomeric adipic anhydride proceeds at a temperature of from about 175° C. to about 225° C., preferably from about 175° C. to about 210° C. at less than about 1 mm Hg pressure. The reaction proceeds with or without a depolymerization catalyst, but Preferably a catalyst is utilized. If the reaction proceeds without a catalyst, approximately 15–20% lower yields result. Preferably the catalyst used in the process of the present invention is zinc acetate dehydrate. The catalyst can be used during the initial stages of the reaction, when the adipic acid and acetic anhydride are initially reacted, as well as during the formation of cyclic monomeric adipic anhydride, which is also the point at which the excess acetic anhydride and excess acetic acid are distilled. The level of depolymerization catalyst utilized is from about 0.5% to about 2% by weight of adipic acid, preferably from about 0.5% to about 1.5%.

The percent purity of cyclic monomeric adipic anhydride is at least about 85%, preferably at least about 90%, more preferably at least about 95%. Below 85%, excessive by-products such as diamides, etc., are produced during the subsequent condensation reaction (b). This percent purity can be obtained by a distillation step at a temperature of about 180° C. to about 215° C. under vacuum. This temperature varies depending on the pressure used.

In the next step of the process, the condensation reactant having a primary active hydrogen is added to the cyclic monomeric adipic anhydride to form the corresponding mono-condensation derivative at a temperature low enough to minimize the formation of di-condensation impurities. The temperature is from 0° C. to about 40° C., preferably from about 10° C. to about 30° C., more preferably from about 20° C. to about 30° C.. If the temperature exceeds 40° C., the carboxylic acid group of mono-nonylamide of adipic acid, or other mono-condensation derivative of adipic acid, may react with any unreacted or excess amine. The resulting amine salt undergoes dehydration upon heating to form diamide. The condensation reactant is selected from the group consisting of: hydrazines; amines; thiol salts; phenoxy salts; alcohols; and mixtures thereof. Preferably, the condensation reactant is a primary or secondary amine having an alkyl group with from 1 to about 20 carbon atoms, and more preferably the condensation reactant is n-nonyl amine.

The molar ratio of cyclic monomeric adipic anhydride to the condensation reactant is from about 1:1 to about 1:0.7, preferably from about 1:1 to about 1:0.9, but is more preferably about 1:1.

The molar ratio of amine should not exceed that of the cyclic monomeric adipic anhydride because excess amine causes the formation of diamide, as described below.

Preferred amines employed in the process of this invention are primary and secondary amines containing either straight or branched chain alkyl groups. Typically, the primary amine contains from 1 to about 20 carbon atoms, preferably from about 6 to about 12 carbon atoms. Such preferred amines are commercially available. Typical amines include hexylamine, heptylamine, octylamine, nonylamine, decylamine, dodecylamine and undecylamine. The linear or straight chaid alkyl amines are preferred because the final amido acids will have higher melting points than branched chain amido acids.

Examples of other condensation reactants, hydrazines, thiol salts, phenoxy salts and alcohols include: N,N-dimethylhydrazine; sodium nonyl mercaptide; sodium phenyl mercaptide (sodium thiophenol), sodium phenoxide, and $C_1$–$C_{20}$ linear or branched alcohols, respectively.

Preferably, the process of the present invention provides from about 85% to about 100% conversion to the mono-condensation derivative of adipic acid.

The use of a non-reactive solvent, such as methylene chloride, when adding the condensation reactant to the cyclic monomeric adipic anhydride, reduces viscosity, reduces diamide impurity, and dissipates heat from the reaction. Therefore, the use of a solvent is preferred. Heat dissipation by the solvent lowers the overall reaction temperature and therefore reduces the formation of diamide. The diamide results from the reaction of the carboxylic acid group of mono-nonylamide of adipic acid, or other mono-condensation derivative of adipic acid, with any unreacted or excess amine. The resulting amine salt of the carboxylic acid group undergoes dehydration upon heating to form a diamide product. If a solvent is not used, heat should be dissipated another way.

By lowering the viscosity, the solvent will also allow better interaction and/or contact among reactants.

The mono-condensation products of the present invention can be used, e.g., as surfactants and/or to prepare bleaching agents such as amidoperoxyacid or the salts thereof useful for bleaching fabrics, hard surfaces and other substrates. These products are excellent precursors to bleaching agents due to their reduced level of metal ions or metals. Metals and metal ions can be deleterious to peroxyacids because they catalyze the decomposition of the peroxygen group. Preferred amidoperoxyacid bleaching agents which can be made by the process of the present invention have the formula:

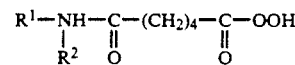

wherein $R^1$ is an alkyl group containing from about 1 to about 20 carbon atoms. Preferably, $R^1$ is an alkyl group containing from about 6 to about 12 carbon atoms. $R^2$ is H or an alkyl group containing from about 1 to about 20 carbon atoms, preferably from 6 to about 12 carbon atoms. Fully formulated liquid bleaches typically contain from about 5% to about 20%, preferably from about 7% to about 15%, by weight of the amidoperoxyacid bleach. Gel compositions typically contain higher levels of the bleach.

Most preferred is the mono-nonylamide of peroxyadioic acid ("NAPAA"). Another name for NAPAA is 6-(nonylamino)-6-oxo-caproic acid. The chemical formula for NAPAA is:

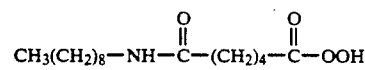

The molecular weight of NAPAA is 287.4.

The amidoperoxyacid obtained is contacted with a phosphate buffer solution at a pH between about 3.5 and 6, preferably between about 4 and 5, according to U.S. Pat. No. 4,909,953, Sadlowski et al., issued Mar. 20, 1990, which is incorporated herein by reference.

Other agents for storage stabilization or exotherm control can be added to the amidoperoxyacid before incorporation into the final product. For example, boric acid, an exotherm control agent disclosed in U.S. Pat. No. 4,686,063, Burns, issued Aug. 11, 1987, and incorporated herein by reference, can be mixed with the amidoperoxyacid (which has been washed in phosphate buffer) in about a 2:1 peracid:boric acid ratio. The phosphate buffer washed amidoperoxyacid can also be mixed with appropriate amounts of dipicolinic acid and tetrasodium pyrophosphate, a chelating stabilization system. Chelants can optionally be included in the phosphate buffer before contact with the wet cake.

NAPAA can be prepared by, for example, first reacting NAAA (mono-nonylamide of adipic acid), sulfuric acid, and hydrogen peroxide. The reaction product is quenched by addition to ice water followed by filtration, washing with distilled water, and final suction filtration to recover the wet cake. Washing can be continued until the pH of the filtrate is neutral.

Small particle size NAPAA agglomerates are desirable to increase the amount of effective bleach which is in the wash solution and thereby improve bleaching/cleaning of fabrics in the wash. This is particularly useful in a hard water wash, i.e., wash water with more than about 6 grains of hardness, because hardness, specifically calcium ions, has been seen to interfere with the effective use of available oxygen (AvO) from NAPAA with larger particle size. While not meaning to be bound by theory, it is believed that the calcium ions in the hard water surround large NAPAA particles, i.e., greater than about 300 microns, and interfere with the dissolution of the NAPAA, and that the smaller (about 0.1-260 microns) NAPAA particles dissolve rapidly in the wash water with minimal interference from the hardness ions. Small NAPAA particles are preferably recovered by quenching in water with high shear applied, e.g., rapid stirring, during addition of the NAPAA solution to water. Other known means of achieving small particle size can be used as appropriate. The NAPAA is then rinsed with water to remove excess sulfuric acid.

The preferred average particle size of the NAPAA is 0.1 to 260 microns and is a function of the amount of shear applied. The average particle size is preferably from about 10 to about 100 microns, preferably from about 30 to about 60 microns.

All percentages and parts herein are by weight unless otherwise specified. All ratios are molar ratios unless otherwise specified. The following exemplifies but does not limit the present invention.

EXAMPLE 1

A small quantity of cyclic monomeric adipic anhydride (about 60.2 gms and at least about 85% purity) is prepared by the following procedure. This will later be converted to nonylamide of adipic acid.

Starting materials:
about 306 gms (3 moles) (4.40 to 1 molar ratio) acetic anhydride (Fisher #902418) (mol. wt. 102.1);
about 100 gms (0.68 moles) adipic acid (Aldrich #12528 EY) (mol. wt. 146.1);
about 1.0 gm zinc acetate (dihydrate) (Aldrich #14526 PX) (mol. wt. 219.5).

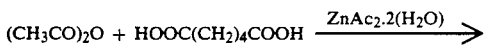

monomeric adipic anhydride
+
polymeric adipic anhydride
+
acetic anhydride
+
acetic acid ↓ heat/vacuum

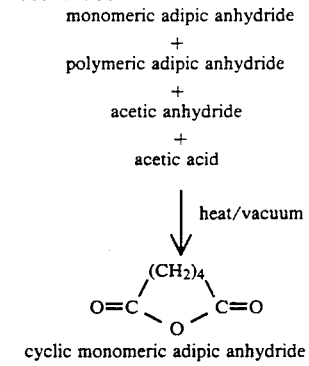

cyclic monomeric adipic anhydride

Procedure:
1. Assemble a one-liter reaction flask with the following: overhead electric stirrer; cold water condenser; $N_2$ inlet adapter; heating mantle; temperature controller; and Hg thermometer.
2. Add about 100 gms adipic acid into the flask along with 300 gms acetic anhydride and about 1.0 gm zinc acetate dehydrate. (Note: The presence of zinc acetate (dihydrate) in the initial stages of the reaction will slow down polymerization.)
3. Blanket the flask with a slight $N_2$ flow and place a drying tube over the condenser outlet.
4. Heat the solution to reflux and allow the reaction to proceed ~7 hrs. (Note: Zinc acetate remains out of solution.)
5. Cool the reaction products to room temperature and leave under a $N_2$ blanket overnight.
6. The next day, prepare the apparatus for distillation and distill over the excess acetic acid/acetic anhydride using vacuum distillation (120° C.; partial vacuum).
7. After removal of the excess reactant, remove the cold water condenser and convert the apparatus for short path distillation.
8. Place the reaction flask under full vacuum (<1 mm Hg) and slowly raise the temperature to ~215° C.
9. Collect the bulk of the cyclic monomeric adipic anhydride between about 180° C. and 210° C. (about 69.2% yield with about 60.2 gms isolated of at least 85% pure cyclic monomeric adipic anhydride).
10. The product from above was diluted with ~200 mls methylene chloride before it had a chance to solidify.

EXAMPLE 2

The cyclic monomeric adipic anhydride of Example 1 is converted to nonylamide of adipic acid by the following procedure:

Starting materials:
about 134.7 gms (0.94 moles) nonyl amine (mol. wt. 143)
about 60.2 gms (0.47 moles) cyclic monomeric adipic anhydride
(mol. wt. 128)

Reaction:

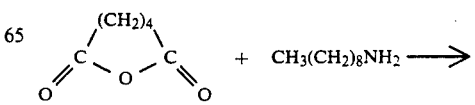

-continued

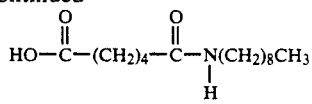

Procedure:
1. Dilute about 134.7 gms nonyl amine into about 200 mls methylene chloride; transfer this solution to a one-liter reaction flask.
2. Transfer about 60.2 gms of cyclic monomeric adipic anhydride solution into a dropping funnel positioned over the reaction flask.
3. Chill the nonyl amine solution to about 0° C. via an ice-MeOH bath.
4. Slowly add (dropwise) the cyclic monomeric adipic anhydride solution over ~2 hrs; maintain the temperature between 0°-30° C. via the ice bath.
5. After complete addition of the cyclic monomeric adipic anhydride, allow the solution to react at room temperature.

This procedure produces about 127.4 gms of mono-nonylamide of adipic acid (mol. wt. 271).

EXAMPLE 3

The mono-nonylamide of adipic acid of Example 2 is treated as follows:
1. Dilute the crude reaction mixture with ~800 mls methylene chloride.
2. Wash the methylene chloride solution two times with dilute HCl solution and two times with warm water (saturated NaCl used to break emulsion).
3. Separate and dry the methylene chloride over $MgSO_4$.
4. Evaporate the excess solvent.
5. Crystallize the residue from above from petroleum ether/MeOH (98/2); filter the crystals through a Buchner funnel; then wash and air dry; yields about 101 gms.
6. Recrystallize the crystals from above from ethyl ether/MeOH (99/1); filter through a Buchner funnel and air dry; yields about 94 gms of the purified mono-nonylamide of adipic acid.

EXAMPLE 4

The cyclic monomeric adipic anhydride of Example 1 is converted to the N,N-dimethylhydrazide of adipic acid by the following procedure:
Starting materials:
about 56.4 gms (0.94 moles) N,N-dimethylhydrazine (mol. wt. 60)
about 60.2 gms (0.47 moles) cyclic monomeric adipic anhydride (mol. wt. 128)
Procedure:
1. Dilute about 56.4 gms (0.94 moles) N,N-dimethylhydrazine into about 200 mls methylene chloride; transfer this solution to a one-liter reaction flask.
2. Transfer about 60.2 gms of cyclic monomeric adipic anhydride solution into a dropping funnel positioned over the reaction flask.
3. Chill the N,N-dimethylhydrazine solution to about 0° C. via an ice-MeOH bath.
4. Slowly add (dropwise) the cyclic monomeric adipic anhydride solution over ~2 hrs; maintain the temperature between 0°-30° C. via the ice bath.
5. After complete addition of the cyclic monomeric adipic anhydride, allow the solution to react at room temperature. After complete reaction the excess N,N-dimethylhydrazine is removed by vacuum distillation.

This procedure produces about 85 gms of adipic acid-N,N-dimethylhydrazide.

EXAMPLE 5

The cyclic monomeric adipic anhydride of Example 1 is converted to the nonyl thiol ester by the following procedure:
Starting materials:
about 128.3 gms (0.7 moles) sodium nonylmercaptide (mol. wt. 182)
about 60.2 gms (0.47 moles) cyclic monomeric adipic anhydride (mol. wt. 128)
Procedure:
1. Combine about 128.3 gms sodium nonylmercaptide into about 200 mls ethyl ether; transfer this mixture to a one-liter reaction flask.
2. Transfer about 60.2 gms of cyclic monomeric adipic anhydride solution into a dropping funnel positioned over the reaction flask.
3. Chill the sodium nonylmercaptide solution/suspension to about 0° C. via an ice-MeOH bath.
4. Slowly add (dropwise) the cyclic monomeric adipic anhydride solution over ~2 hrs; maintain the temperature between 0°-30° C. via the ice bath.
5. After complete addition of the cyclic monomeric adipic anhydride, allow the solution to warm to room temperature and stir overnight.

This procedure produces about 135.4 gms of the thiol ester.

EXAMPLE 6

The thiol ester of Example 5 is treated as follows:
1. Strip off the ethyl ether under vacuum.
2. Dissolve the crude reaction mixture in ~800 mls methylene chloride.
3. Wash the methylene chloride solution two times with dilute HCl solution and two times with warm water (saturated NaCl used to break emulsion).
4. Separate and dry the methylene chloride over $MgSO_4$.
5. Evaporate the excess solvent.
6. Crystallize the residue from above from petroleum ether/MeOH (98/2); filter the crystals through a Buchner funnel; then wash and air dry; yields about 120 gms.
7. Recrystallize the crystals from above from ethyl ether/MeOH (99/1); filter through a Buchner funnel and air dry.

EXAMPLE 7

The cyclic monomeric adipic anhydride of Example 1 is converted to the thiol phenol ester by the following procedure:
Starting materials:
about 68.64 gms (0.52 moles) sodium phenylmercaptide (mol. wt. 132)
about 60.2 gms (0.47 moles) cyclic monomeric adipic anhydride (mol. wt. 128)
Procedure:
1. Dilute about 68.64 gms sodium phenylmercaptide into about 200-400 mls ether; transfer this solution to a one-liter reaction flask.
2. Transfer about 60.2 gms of cyclic monomeric adipic anhydride solution into a dropping funnel positioned over the reaction flask.

3. Chill the sodium phenylmercaptide solution to about 0° C. via an ice-MeOH bath.
4. Slowly add (dropwise) the cyclic monomeric adipic anhydride solution over ~2 hrs; maintain the temperature between 0°-25° C. via the ice bath.
5. After complete addition of the cyclic monomeric adipic anhydride, allow the solution to react at room temperature (over ~2 days) then strip off the solvent under vacuum.

This procedure produces about 111 gms of the phenyl thiol ester of adipic acid.

EXAMPLE 8

The phenyl thiol ester of Example 7 is treated as follows:
1. Dilute the crude reaction mixture, with ~800 mls methylene chloride.
2. Wash the methylene chloride solution two times with dilute HCl solution and two times with warm water (saturated NaCl used to break emulsion).
3. Separate and dry the methylene chloride over MgSO$_4$.
4. Evaporate the excess solvent.
5. Crystallize the residue from above from petroleum ether/MeOH (98/2); filter the crystals through a Buchner funnel; then wash and air dry; yields about 95 gms.
6. Recrystallize the crystals from above from ethyl ether/MeOH (99/1); filter through a Buchner funnel and air dry.

EXAMPLE 9

The cyclic monomeric adipic anhydride of Example 1 is converted to the mono-octyl ester by the following procedure:

Starting materials:
about 62 gms of n-octanol (mol. wt. 130)
about 60.2 gms cyclic monomeric adipic anhydride (mol. wt. 128)

Procedure:
1. Dissolve about 62 gms of n-octanol in about 200 mls methylene chloride; transfer this solution to a one-liter. reaction flask.
2. Transfer about 60.2 gms of cyclic monomeric adipic anhydride solution into a dropping funnel positioned over the reaction flask.
3. Chill the octanol solution to about 0° C. via an ice-MeOH bath.
4. Slowly add (dropwise) the cyclic monomeric adipic anhydride solution over ~2 hrs; maintain the temperature between 0°-30° C. via the ice bath.
5. After complete addition of the cyclic monomeric adipic anhydride, allow the solution to react at room temperature for four hours before removing the solvent.

This procedure produces about 121.3 gms of mono-octylester of adipic acid (mol. wt. 258).

EXAMPLE 10

The mono-octylester of adipic acid of Example 9 is treated as follows:
1. Dilute the crude reaction mixture with ~800 mls methylene chloride.
2. Wash the methylene chloride solution two times with warm water (saturated NaCl used to break emulsion).
3. Separate and dry the methylene chloride over MgSO$_4$.
4. Evaporate the excess solvent. This procedure yields about 115 gms of product.

What is claimed is:
1. A process for preparing mono-condensation derivatives of adipic acid comprising the following steps:
   (a) forming at least about 85% pure cyclic monomeric adipic anhydride by depolymerization and concentration starting from the polymeric adipic anhydride; and
   (b) adding a condensation reactant having a primary active hydrogen to the cyclic monomeric adipic anhydride to form a mono-condensation derivative of adipic acid;
   wherein the molar ratio of cyclic monomeric adipic anhydride to the condensation reactant is from about 1:1 to about 1:0.7.
2. A process according to claim 1 wherein the cyclic monomeric adipic anhydride is at least about 95% pure.
3. A process according to claim 1 wherein the condensation reactant is selected from the group consisting of: hydrazines; amines; thiol salts; phenoxy salts; alcohols; and mixtures thereof.
4. A process according to claim 3 wherein the condensation reactant is a primary or secondary amine.
5. A process according to claim 4 wherein the condensation reactant is a primary or secondary amine having an alkyl group of 6 to 12 carbon atoms.
6. A process according to claim 5 wherein the condensation reactant is n-nonyl amine.
7. A process according to claim 3 wherein the condensation reactant is a hydrazine.
8. A process according to claim 7 wherein the condensation reactant is N,N-dimethylhydrazine.
9. A process according to claim 3 wherein the condensation reactant is a thiol salt.
10. A process according to claim 9 wherein the condensation reactant is sodium nonylmercaptide.
11. A process according to claim 9 wherein the condensation reactant is sodium phenylmercaptide.
12. A process according to claim 3 wherein the condensation reactant is a phenoxy salt.
13. The process according to claim 3 wherein the condensation reactant is an alcohol.
14. The process according to claim 13 wherein the condensation reactant is octanol.
15. A process according to claim 1 wherein step (b) occurs at a low enough temperature to prevent the formation of di-condensation impurities.
16. A process according to claim 15 wherein the temperature is from about 0° C. to about 40° C.
17. A process according to claim 16 wherein the temperature is from about 10° C. to about 30° C.
18. A process according to claim 1 wherein the molar ratio of cyclic monomeric adipic anhydride to the condensation reactant is from about 1:1 to about 1:0.9.
19. A process according to claim 1 wherein the depolymerization of polymeric adipic anhydride occurs via a catalyst.
20. A process according to claim 19 wherein the depolymerization catalyst is zinc acetate at a level of from about 0.5% to about 2%, by weight of adipic acid.
21. A process according to claim 20 wherein the level of zinc acetate is from about 0.5% to about 1.5%, by weight of adipic acid.
22. A process according to claim 1 wherein the cyclic monomeric adipic anhydride is distilled and collected at a temperature of from about 180° C. to about 215° C. under vacuum.

23. A mono-condensation derivative of adipic acid produced by the process of claim 1.

24. The mono-condensation derivative of claim 23 which is mono-nonyl amide of adipic acid.

25. An amidoperoxyacid prepared from a mono-condensation derivative of claim 23 which is a mono-amide of adipic acid.

26. The process according to claim 1 wherein the reaction of Step 1(b) proceeds in the presence of a solvent.

27. The process according to claim 26 wherein the solvent is methylene chloride.

28. A process for preparing at least 85% pure cyclic monomeric adipic anhydride comprising the following steps: (a) depolymerizing polymeric adipic anhydride; and (b) concentrating the resulting cyclic monomeric adipic anhydride; wherein the depolymerization of polymeric adipic anhydride occurs via a catalyst.

29. A process according to claim 28 wherein the concentration is achieved by distillation.

* * * * *

UNITED STATES PATENT AND TRADEMARK OFFICE
CERTIFICATE OF CORRECTION

PATENT NO. : 5,286,879
DATED : February 15, 1994
INVENTOR(S) : James C. Letton and Larry E. Miller It is certified that error appears in the above-identified patent and that said Letters Patent is hereby corrected as shown below:

Col. 3, line 6, "but Preferably" should read -- but preferably --.

Col. 3, lines 9-10, "dehydrate" should read -- dihydrate --.

Col. 3, line 65, "chaid." should read -- chain --.

Col. 4, lines 46-47, "$R^2$i s H" should read -- $R^2$ is H --.

Col. 4, lines 54-55, "peroxyadioic" should read -- peroxyadipic --.

Col. 6, line 24, "dehydrate" should read -- dihydrate --.

Signed and Sealed this

Eleventh Day of February, 1997

Attest:

BRUCE LEHMAN

Attesting Officer

Commissioner of Patents and Trademarks